United States Patent
Hegazi et al.

(10) Patent No.: US 9,869,664 B2
(45) Date of Patent: Jan. 16, 2018

(54) METHOD FOR NON-INTRUSIVE MEASUREMENT OF LOW WATER CONTENT IN OIL

(71) Applicant: Saudi Arabian Oil Company, Dhahran (SA)

(72) Inventors: Ezzat M. Hegazi, Dhahran (SA); Abdul Rahman Zafer Akhras, Dhahran (SA)

(73) Assignee: SAUDI ARABIAN OIL COMPANY (SA)

( * ) Notice: Subject to any disclaimer, the term of this patent is extended or adjusted under 35 U.S.C. 154(b) by 273 days.

(21) Appl. No.: 14/132,093

(22) Filed: Dec. 18, 2013

(65) Prior Publication Data

US 2015/0168368 A1 Jun. 18, 2015

(51) Int. Cl.
*G01N 33/28* (2006.01)
*G01N 21/64* (2006.01)

(52) U.S. Cl.
CPC ......... *G01N 33/2847* (2013.01); *G01N 21/64* (2013.01)

(58) Field of Classification Search
CPC ....... G01N 33/2847; G01N 2021/6417; G01N 2021/6406; G01N 2021/6426; G01N 2021/6495; G01N 2021/6497; G01N 21/64

See application file for complete search history.

(56) References Cited

U.S. PATENT DOCUMENTS

| | | | |
|---|---|---|---|
| 3,500,046 A | 3/1970 | Caldwell | |
| 4,367,440 A | 1/1983 | Mazzagatti | |
| 4,446,370 A | 5/1984 | Gergely | |
| 4,916,940 A | 4/1990 | Mougne | |
| 5,033,289 A | 7/1991 | Cox | |
| 5,296,711 A | 3/1994 | Leonard et al. | |
| 6,407,383 B1 | 6/2002 | Byatt et al. | |
| 6,707,556 B2 | 3/2004 | Turner et al. | |
| 7,839,492 B2 | 11/2010 | Parks, II et al. | |
| 2003/0141459 A1 | 7/2003 | Hegazi et al. | |
| 2007/0237679 A1* | 10/2007 | Hegazi | G01N 21/6402 422/82.08 |

(Continued)

FOREIGN PATENT DOCUMENTS

DE 102012100794 B3 2/2013

OTHER PUBLICATIONS

Anonymous; Laser Invenition is Used to Fingerprint Oil; Aramco ExPats Articles; Feb 3, 2010; pp. 1-2.*

(Continued)

*Primary Examiner* — Peter Macchiarolo
*Assistant Examiner* — Nathaniel Kolb
(74) *Attorney, Agent, or Firm* — Bracewell LLP; Constance Gall Rhebergen

(57) ABSTRACT

The present invention relates to a method and apparatus for determining trace amounts of water in oil, including the steps of obtaining a blended sample of a low water content fluid including an amount of water and an amount of oil, transferring a portion of the blended sample to a cuvette to create a measurement sample, covering a viewing surface of the cuvette with an opaque sheet with a slit, providing a barrier with a fixed opening between a laser source and a laser-receptive surface of the cuvette, transmitting a pulsed laser beam from the laser source into the cuvette; inducing fluorescence in the measurement sample, focusing the fluorescence through a collecting lens and transmitting the fluorescence to a spectrometer, and measuring the fluorescence with the spectrometer by dispersing the fluorescence with a spectrograph and intensifying the fluorescence with an intensified charge coupled device.

10 Claims, 5 Drawing Sheets

(56) References Cited

U.S. PATENT DOCUMENTS

| | | | |
|---|---|---|---|
| 2008/0035858 A1 | 2/2008 | Hegazi | |
| 2011/0151576 A1* | 6/2011 | Perfect | G01N 21/643 |
| | | | 436/172 |
| 2011/0194105 A1 | 8/2011 | Lafrancois et al. | |
| 2011/0303834 A1* | 12/2011 | Hegazi | G01N 21/6402 |
| | | | 250/252.1 |
| 2012/0043477 A1* | 2/2012 | Hegazi | G01N 21/274 |
| | | | 250/459.1 |
| 2013/0107251 A1 | 5/2013 | Hegazi et al. | |
| 2013/0161243 A1* | 6/2013 | Kanomata | G01N 30/74 |
| | | | 210/85 |

OTHER PUBLICATIONS

PCT International Search Report and the Written Opinion; dated Mar. 20, 2015; International Application No. PCT/US2014/070028; dated Dec. 12, 2014.

Anonymous; Laser Invention Is Used to Fingerprint Oil; Aramco ExPats Articles; Feb. 3, 2010; pp. 1-2; Retrieved from the Internet: URL:http://www.aramcoexpats.com/articles/2010/02/laser-invention-is-used-to-fingerprint- oil/[retrieved on Oct. 25, 2011].

Hug, W. F., et al., Water and Surface Contamination Monitoring Using Deep UV Laser Induced Native Fluorescence and Raman Spectroscopy; SPIE Proceedings; Oct. 17, 2006; pp. 1-2; vol. 6378.

Miller, D. J., et al., Optical Studies of Coalescence in Crude Oil Emulsions; Journal of Petroleum Science and Engineering; Feb. 1993; pp. 1-8; vol. 9, No. 1; Elsevier Science Publishers B. V., Amsterdam.

Moise, N., et al., Meausring of Water and Soil Contamination with Oil Components Using Laser-Induced Fluorescence Transmitted Through Optical Fibers; SPIE Proceedings; Mar. 8, 1995; pp. 1-2; vol. 2461.

Pal, R., et al., Techniques for Measuring the Composition (oil and water content) of Emulsions—a State of the Art Review; Colloids and Surfaces—A: Physicochemical and Engineering Aspects; May 11, 1994; pp. 141-193; vol. 84, Nos. 2/3; Elsevier Science B. V.

* cited by examiner

METHOD FOR NON-INTRUSIVE MEASUREMENT OF LOW WATER CONTENT IN OIL

FIELD OF THE INVENTION

The invention relates to a method for determining water content in petroleum fluids. Specifically, the invention relates to a non-intrusive method for rapidly determining the water content in petroleum fluids based on spectroscopic measurements of laser-induced fluorescence emitted from a water-oil mixture.

BACKGROUND OF THE INVENTION

Analytical testing for contaminants in a petroleum fluid is an important step in many industrial processes. Contaminants can be in the form of small amounts of other types of fuels which have remained, for example, in multi-purpose pipelines or refined oil storage tanks. Contaminants can be in the form of small amounts of the same fuel but having different sulfur contents, which commonly happens in diesel fuel distribution operations and storage. The contaminants can also be in the form of weathered fuels mixed with fresh ones or in the form of some chemicals that cannot readily be identified.

Water as a contaminant is a concern in certain applications. The contamination of jet fuel by condensation water is known to be a serious safety concern in the aviation industry and was found to be the cause of several helicopter crashes in hot and humid tropical countries.

Common analytical methods of testing for contaminants include using infrared absorption, ultra violet (UV) absorption, and nuclear magnetic resonance, but each of these contain drawbacks.

Liquid hydrocarbon fuels (e.g., jet fuel, gasoline, and diesel fuel) can be characterized by fluorescence emission spectra of distinct shapes when excited with ultraviolet light. When such fuels become contaminated or blended with another type of fuel their spectral shapes suffer alterations depending on the fluorescence spectral/temporal characteristics of the contaminants. In most of these cases, the contaminants in the hydrocarbon fuels can be identified by making a comparison in the shapes of the fluorescence emission spectra between the contaminated and the uncontaminated samples. In one method the identification of the oil is made by direct visual comparison of the sample's fluorescence emission spectrum with the same spectra of possible source samples, all being excited using ultraviolet radiation at 254 nm. In other words, to perform spectral comparisons, whether visual or numerical, measurements must first be performed on a reference sample, or on a set of reference samples, in order to generate the necessary reference data to which the measurements from the unknown sample will be compared. In many cases, the needed information will not be only the type of the contaminants but also their volume ratios in the blend, i.e., their concentrations. This, in turn, necessitates the additional steps of preparing sets of standard blends with known concentrations and performing measurements on them to produce the necessary calibration curves.

A more difficult contaminant to quantify or even to identify is water. Water does not fluoresce. Known fluorescence-based methods are primarily adapted for measurement of oil-in-water emulsions, for the range of volumetric water concentrations from approximately 50% up to 99%. These methods are not well-adapted for the different design parameters facing water-in-oil measurement for water concentrations in the range from 0.01% up to a few percent by volume, because water does not fluoresce, the prominent fluorescence signal from the oil will not be appreciably affected by the presence of only minute amounts of water. The inability to accurately measure low concentrations of water in oil means there is no good way of measuring water concentration locally inside a water-in-oil emulsion flow domain. Consequently, there is almost no experimental data on water concentration gradients inside flowing emulsion layers available to the scientific community. Such data would be useful to better understand the behavior of flowing emulsions and the development of models describing the formation and separation of flowing emulsions.

In addition, none of the methods known in the prior art describe a direct correlation between laser-induced fluorescence intensity measurements of oil in a water-in-oil mixture and the water content in the mixture.

The main techniques for accurate water concentration measurement in the volumetric range between 0.01% and about 1% are based on the titration of a chemical reactant (e.g., $I_2$ reacts quantitatively with $H_2O$ present in the oil). This and other techniques involving sampling, dilution, and several successive manipulations in a laboratory environment make them impractical for real-time process monitoring applications as needed in crude oil production facilities as well as in oil refineries and petrochemical plants, because they are intrusive to flowing fluids. For example, one method known in the prior art assesses a multiphase mixture sample including an aqueous phase by using a fluorescing dye. The addition of a detection molecule in the fluorescing dye, which fluoresces on contact with the particular phase to be assessed, is intrusive to the flow by requiring the dye to be added to the flow in order to measure water in oil samples. These methods are also ill suited to measuring local water content in a tank or other holding device.

Therefore, a need exists for an apparatus capable of determining trace amounts of water in oil that can be submerged at different depths in a fuel storage tank to detect water contamination and measure water concentration at different heights, that can be installed in-line with the process stream at a suitable location in the process or installed on a by-pass line, that is a non-intrusive method of measuring water concentration in a fluid having a low water content, and a method and system capable of rapidly and non-intrusively detecting trace amounts of water in localized regions within a volume of oil-containing fluid.

SUMMARY OF THE INVENTION

The present invention relates to a method for determining trace amounts of water in oil, including the step of obtaining a blended sample of a low water content fluid, where the low water content fluid includes an amount of oil and an amount of water distributed as water droplets with an average diameter. The method also includes the steps of transferring a portion of the blended sample to a cuvette to create a measurement sample. The viewing surface of the cuvette is adjacent to a laser-receptive surface of the cuvette and has an opaque sheet containing a slit to form a covered side. The method also includes the step of transmitting a pulsed laser beam through the laser-receptive surface of the cuvette. In a further step, the pulsed laser beam induces fluorescence in a fluorescence spectrum of the measurement sample, and the fluorescence emits from the slit in the opaque sheet on the covered side of the cuvette. In a further step, the fluorescence is focused through a collecting lens located between the cuvette and a spectrometer, at which point the fluorescence is measured with the spectrometer. The spectrometer includes a spectrograph coupled with an intensified charge coupled device. The fluorescence is measured by dispersing the fluorescence with the spectrograph and intensifying the fluorescence with the intensified charge coupled device.

In certain embodiments of the present invention, the method further includes the steps of providing a barrier located between the laser source and the laser-receptive surface of the cuvette, the barrier defining a fixed opening and transmitting the pulsed laser through the fixed opening prior to transmitting the laser through the laser-receptive surface of the cuvette.

In certain embodiments of the present invention, the average diameter of the water droplets is in a range between 30 μm and 70 μm.

In certain embodiments, the pulsed laser beam has a wavelength of 266 nm.

In certain embodiments, the fluorescence spectrum is in a range between 280 nm and 450 nm.

In certain embodiments, the pulsed laser beam pulses for a temporal span of 6 ns/pulse at an energy of 20 mJ/pulse.

In certain embodiments, the slit is 0.5 mm wide.

In certain embodiments, the slit is 4 mm from an edge of the cuvette.

In certain embodiments, the oil is jet fuel.

In certain embodiments, the method further includes the steps of collecting a sample of the low water content fluid and blending the sample to create the blended sample.

In certain embodiments, the method also includes the steps of taking additional portions from the blended sample at different locations of the blended sample and measuring the fluorescence of those portions with a spectrometer, where the measurements of the blended sample portions give the ability to map the entire blended sample.

In another aspect of the invention, the present invention relates to an apparatus for determining trace amounts of water in oil. The apparatus includes the cuvette with the laser-receptive surface and with the viewing surface. The cuvette is configured to hold the blended sample of low water content fluid containing the amount of water and the amount of oil. The amount of water in the blended sample is distributed as water droplets having an average diameter. The apparatus also includes the opaque sheet with the slit, the opaque sheet configured to block transmission of fluorescence through a portion of the viewing surface of the cuvette, and the slit configured to pass fluorescence from the cuvette. The apparatus further includes the laser source configured to direct the pulsed laser beam through the laser-receptive surface of the cuvette, the pulsed laser beam configured to induce fluorescence in the fluorescence spectrum of the blended sample. The apparatus further includes the collecting lens configured to collect and transmit the fluorescence to the spectrometer. The spectrometer is configured to measure the fluorescence that passes through the slit and includes the spectrograph configured to disperse the fluorescence and the intensified charge coupled device configured to intensify the fluorescence.

In certain embodiments of the present invention, the apparatus further includes a barrier defining a fixed opening, the fixed opening located between the cuvette and the laser source, wherein the fixed opening is configured to reduce a diameter of the pulsed laser beam. In certain embodiments of the present invention, the average diameter of the water droplets is in a range between 30 μm and 70 μm. In certain embodiments of the present invention, the pulsed laser beam has a wavelength of 266 nm. In certain embodiments of the present invention, the fluorescence spectrum is in a range between 280 nm and 450 nm. In certain embodiments of the present invention, the spectrograph is located between the collecting lens and the intensified charge coupled device, and wherein the intensified charge coupled device is synchronized with the pulsed laser beam. In certain embodiments of the present invention, the pulsed laser beam pulses for a temporal span of 6 ns/pulse at an energy of 20 mJ/pulse. In certain embodiments of the present invention, the slit is 0.5 mm wide. In certain embodiments of the present invention, the slit is 4 mm from an edge of the cuvette.

BRIEF DESCRIPTION OF THE DRAWINGS

These and other features, aspects, and advantages of the present invention will become better understood with regard to the following descriptions, claims, and accompanying drawings. It is to be noted, however, that the drawings illustrate only several embodiments of the invention and are therefore not to be considered limiting of the invention's scope as it can admit to other equally effective embodiments.

DETAILED DESCRIPTION OF THE INVENTION

While the invention will be described with several embodiments, it is understood that one of ordinary skill in the relevant art will appreciate that many examples, variations and alterations to the apparatus and methods described herein are within the scope and spirit of the invention. Accordingly, the exemplary embodiments of the invention described herein are set forth without any loss of generality, and without imposing limitations, on the claimed invention.

Figure 1:
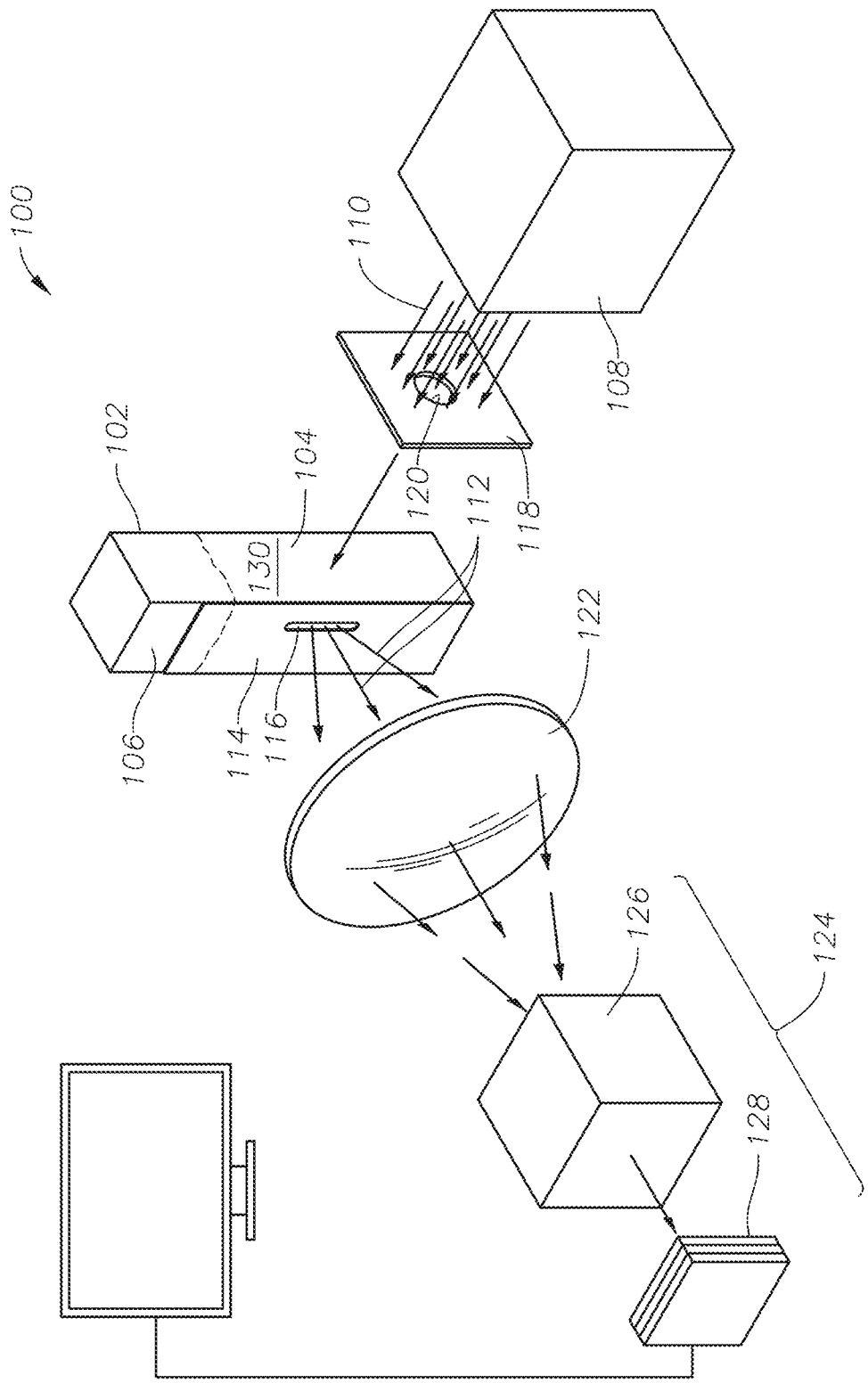
FIG. 1 is a pictorial representation of an apparatus capable of detecting the presence of trace amounts of water using spectroscopic absorption of laser-induced fluorescence, according to one embodiment of the present invention.

FIG. 1 depicts apparatus 100 for determining trace amounts of water in oil. Apparatus 100 includes cuvette 102 with laser-receptive surface 104 and with viewing surface 106. Cuvette 102 can be any suitable vessel allowing measurement sample 130 to be accurately measured. Exemplary materials for cuvette 102 include quartz, glass, plastic, metal, ceramic material, and other like materials. In at least one embodiment, cuvette 102 is a quartz cuvette capable of holding about 3 mL to about 4 mL of fluid. In a further embodiment, cuvette 102 is in the shape of a rectangular prism. Laser-receptive surface 104 and viewing surface 106 are positioned adjacent to one another. Laser-receptive surface 104, viewing surface 106, and cuvette 102 can be made of the same material or of different materials. Laser-receptive surface 104 is capable of allowing electromagnetic radiation emitted from laser source 108, such as pulsed laser beam 110, to pass into cuvette 102. In accordance with at least one embodiment, pulsed laser beam 110 is transmitted through laser-receptive surface 104 and into cuvette 102, causing a laser-induced fluorescence to emit from measurement sample 130. Viewing surface 106 is substantially transparent and capable of allowing fluorescence 112 to emit from cuvette 102. The angle between laser-receptive surface 104 and viewing surface 106 allows the laser beam to penetrate inside cuvette 102 for a distance which provides an interaction within a small volume rather than being a mere surface interaction. The angle between laser-receptive surface 104 and viewing surface 106 can be between about 60° and about 120°. In one embodiment, laser-receptive surface 104 and viewing surface 106 are configured to form a 90° angle.

One having skill in the art will appreciate that electromagnetic radiation can be used interchangeably with light, UV light, electromagnetic wave, and fluorescence emitted to describe electromagnetic energy traveling in the form of a wave.

Cuvette 102 is configured to hold the blended sample of the low water content fluid. The low water content fluid includes an amount of oil and an amount of water. The low water content fluid could contain any amount of water in an amount of oil, so long as the low water content fluid forms a stable emulsion, where there is limited or no separation of the amount of water from the amount of oil. In certain embodiments, the amount of water is less than about 3% by volume. In accordance with one embodiment, the amount of water in the tow water content fluid is between a trace amount, such as between about 0.001% and about 1% by volume. The amount of water in the blended sample is distributed as water droplets in an oil phase. In certain embodiments, the water droplets have an average diameter between about 30 µm and about 70 µm. In at least one embodiment, the water droplets have an average diameter of about 50 µm. Water droplet size is measured using focused beam reflectance measurement (FBRM) technology.

Apparatus 100 further contains opaque sheet 114 with slit 116. Opaque sheet 114 is configured to cover or to block transmission of light from at least a portion of viewing surface 106 of cuvette 102. In some embodiments, opaque sheet 114 is configured to be applied to viewing surface 106 of cuvette 102. Exemplary materials for opaque sheet 114 include any metal, polymer, organic, ceramic, or like material. Alternately, opaque sheet 114 can be any coating capable of inhibiting the transmission of the laser-induced fluorescence emitted from measurement sample 130 or any opaque material for the cuvette viewing surface. In one embodiment, opaque sheet 114 is a thin metallic material. Slit 116 is configured to ensure that fluorescence 112 passes only from a particular location within cuvette 102. Slit 116 provides a window or transparent surface through which fluorescence 112 passes. Slit 116 can be of any size operable to control fluorescence 112 emitted from viewing surface 106 of the cuvette. The size of the slit determines which part of the fluorescence is detected. The size of slit 116 is chosen to be approximately proportional to the diameter of pulsed laser beam 110 and larger than the water droplets average diameter. The height of slit 116 can be between about 0.5 cm and about 1.5 cm. In at least one embodiment, slit 116 has a height of 1 cm. The width of slit 116 can be between about 0.2 mm and 2.0 mm. In at least one embodiment, slit 116 has a width of about 0.5 mm. In at least one embodiment, the size and position of the slit 116 is fixed for all measurements. One of skill in the art will appreciate that slit 116 can be disposed anywhere on opaque sheet 114 such that the position of slit 116 relative to the edge of cuvette 102 allows for volume interaction between pulsed laser beam 110 and the sample in cuvette 102, while not being so far from the edge that the fluorescence signal is attenuated due to absorption. In at least one embodiment, slit 116 is located about 4 mm from the edge of cuvette 102 joining laser-receptive surface 104 and viewing surface 106. Slit 116 can be any shape capable of passing fluorescence 112 from cuvette 102. Exemplary shapes include, rectangle, square, oval, circle, and other polygons.

Laser source 108 is configured to direct electromagnetic radiation in the form of a laser beam from laser source 108 to laser-receptive surface 104. Laser source 108 generates electromagnetic radiation of any frequency in accordance with any of the laser-induced fluorescence methods well-known in the art. Laser source 108 can be a continuous laser generating a continuous laser beam, a Q-switched laser generating a pulsed laser beam, or a continuous laser with a chopper generating a pulsed laser beam. In at least one embodiment of the present invention, laser source 108 generates pulsed laser beam 110 in the form of a laser pulse directed through laser-receptive surface 104 of cuvette 102. In at least one preferred embodiment, laser source 108 uses a Q-switch to generate a Q-switched laser beam as pulsed laser beam 110. Exemplary embodiments of Q-switches are acousto-optic modulators, electro-optic modulators, spinning mirrors, saturable absorbers, and the like. Pulsed laser beam 110 is configured to induce fluorescence in measurement sample 130 by irradiating the sample within cuvette 102. Pulsed laser beam 110 can contain light having any wavelength capable of inducing fluorescence in measurement sample 130. In some embodiments, pulsed laser beam 110 has a wavelength in a range between about 250 nm and about 400 nm. According to one embodiment, pulsed laser beam 110 has a wavelength of about 266 nm. Pulsed laser beam 110 can have an energy of between about 1 mJ and about 100 mJ. In one embodiment, pulsed laser beam 110 pulses for a temporal span of about 6 ns/pulse at an energy of about 20 mJ/pulse. The span between pulses can range from about 0.05 s to about 0.1 s. One of skill in the art will appreciate that the span of each pulse and the span between pulses can be designed based on the nature of fluorescence of the sample and the laser being used.

In some embodiments of the present invention, barrier 118 is disposed between laser source 108 and laser-receptive surface 104 of cuvette 102. With regard to barrier 118, exemplary materials include metals, polymers, organic materials, ceramics, and any other material capable of blocking the laser beam. In at least one embodiment of the present invention, barrier 118 controls the size of the laser beam from laser source 108. Barrier 118 includes fixed opening 120 through which the laser beam can pass. Fixed opening 120 ensures that the diameter of the laser beam going through it has a fixed and uniform diameter. Fixed opening 120 can include a single aperture or a plurality of apertures allowing one or more laser beams to pass into cuvette 102 at multiple locations. In certain embodiments, fixed opening 120 is disposed on barrier 118 at a location substantially concentric with a cross-section of the laser beam. Barrier 118 can be used to condition the diameter of the laser beam by reducing the cross-sectional area of the laser beam that passes through fixed opening 120. In some embodiments, fixed opening 120 is circular in shape. The size of fixed opening 120 is determined based on the water droplet average size in the fluid sample. The size of fixed opening 120 is fixed to be in the range of about 50 to about 200 times the water droplet average size. In one embodiment, the diameter of fixed opening 120 is about 5 mm.

In at least one embodiment of the present invention, apparatus 100 is in the absence of barrier 118, such that laser source 108 controls the size of the laser beam.

Spectrometer 124 is configured to measure the fluorescence that passes through slit 116. Spectrometer 124 can be any instrument capable of separating and measuring at least one property of an incoming electromagnetic wave. In one embodiment, spectrometer 124 includes any suitable detector in conjunction with an optical filter in 360-370 nm range. Exemplary optical filters include photomultipliers and charge coupled devices. In at least one embodiment of the present invention, spectrometer 124 includes spectrograph 126 coupled with a charge coupled device. In some embodiments, spectrograph 126 is located between collecting lens 122 and the charge coupled device. In certain embodiments, the charge coupled device is intensified charge coupled device (ICCD) 128. Spectrometer 124 measures the intensity of fluorescence 112 across the fluorescence spectrum corresponding to a range of wavelengths at which measurement sample 130 fluoresces. The fluorescence spectrum of measurement sample 130 can be affected by the diameter of the water droplets, the make-up of the amount of oil in the low water content fluid, and the wavelength of pulsed laser beam 110. In some embodiments, the fluorescence spectrum of measurement sample 130 is in a range between about 280 nm and about 450 nm depending on the type of oil. Spectrograph 126 can disperse fluorescence 112 over the fluorescence spectrum of the blended sample. In some embodiments, spectrograph 126 disperses fluorescence 112 with a resolution of about 3 nm. Dispersed fluorescence from spectrograph 126 can be intensified and displayed by activating ICCD 128. ICCD 128 can receive the dispersed fluorescence and output an intensified signal capable of being displayed on a monitor. In at least one embodiment, ICCD 128 is synchronized with the Q-switch of pulsed laser beam 110, such that ICCD 128 is only active during a time window corresponding to the laser pulse generated by laser source 108. It is important to maintain a constant voltage across the charge coupled device to ensure that the fluorescence intensities of additional portions taken from the blended sample are all measured relative to the same reference point.

As depicted in FIG. 1, collecting lens 122 can be disposed between viewing surface 106 and spectrometer 124. Collecting lens 122 collects and focuses fluorescence 112 emitted from slit 116 by refracting and transmitting electromagnetic radiation to spectrometer 124. Collecting lens 122 can be a single lens or a plurality of lenses. With respect to collecting lens 122, exemplary materials include glass, polymers, quartz, sapphire, fused silica, and the like. In at least one embodiment, collecting lens 122 is made of quartz. In some embodiments, the optical surfaces of collecting lens 122 are substantially orthogonal to the vector formed between the center of slit 116 and the center of a detector of spectrometer 124. Collecting lens 122 can be configured to transmit a greater amount of fluorescence 112 emitted from slit 116 to spectrograph 126 than would otherwise be possible.

In some embodiments, apparatus 100 is installed in-line with a process stream. Alternately, apparatus 100 can be installed on a bypass line. The sample can be transferred to a measurement vessel either in-line with a process stream or on a bypass line using a valve assembly prior to performing the method described below. In some embodiments, apparatus 100 is portable.

In another aspect, the invention provides a method for determining trace amounts of water in an oil-containing fluid, such as an amount of water between about 0.001% and about 3% by volume. The method includes the steps of obtaining the blended sample of the low water content fluid and transferring a portion of the blended sample to cuvette 102. Pulsed laser beam 110 is transmitted through laser-receptive surface 104 of cuvette 102, thereby inducing fluorescence in the fluorescence spectrum of measurement sample 130. Fluorescence 112 is emitted through slit 116 on the covered side of cuvette 102 and focused through collecting lens 122. Fluorescence 112 is then measured with spectrometer 124 by dispersing the fluorescence with spectrograph 126 and intensifying the fluorescence with the charge coupled device, which can be ICCD 128. In some embodiments, multiple portions of the blended sample are sequentially transferred to cuvette 102, providing the ability to map the overall water distribution of the entire blended sample.

The method can be performed non-intrusively by performing the method of the invention described below without imparting any changes in the characteristics of the low water content fluid during measurement. In some embodiments, the blended sample of the low water content fluid is obtained by accomplishing the steps of collecting the sample of the low water content fluid and blending the sample to create the blended sample. The low water content fluid can include an amount of oil and an amount of water in a range between about 0.001% and about 3% by volume. The sample of the low water content fluid can be any source of oil-containing fluid. Exemplary oil-containing fluids include crude oil, gasoline, diesel, alcohols, kerosene, jet fuel, liquefied petroleum gas, liquefied natural gas, and any other liquid hydrocarbons. In one embodiment, the sample is kerosene jet fuel. The sample can be collected from a process stream or a storage vessel in a production facility, refinery, processing facility, distillation facility, petrochemical plant, oil-water separator, reservoir, production well, fuel storage tank, or any other location where an oil-containing fluid is present. In some embodiments, the sample is collected directly from a process stream by an in-line apparatus. Alternately, the sample can be collected from a bypass line. In accordance with at least one embodiment, the sample is collected from a multiphase mixture fluid flow, such as a water-in-oil emulsion flow. The sample can be collected in a container. Exemplary containers include beakers, flasks, cups, bottles, jars, drums, storage tanks, fuel tanks, and other like repositories. In one embodiment, the sample is collected in a beaker having a volume of about 1000 mL.

In some embodiments, the method also includes the step of blending the sample to create the blended sample with an amount of water distributed as water droplets. Blending the sample has a shearing effect on the sample, thereby emulsifying the fluid phases within the sample. The sample can be blended by mixing, shaking, stirring, blending, heating, atomization, emulsifying, or any other known method to create a blended mixture. In at least one embodiment, the sample is blended using a handheld blender. The average diameter of the water droplets is an important parameter to keep uniform, because water is a weak fluorescing material when excited with UV light, and different droplet sizes tend to alter the fluorescence patterns of the sample. The water droplets in the blended sample can have an average diameter in a range between 30 µm and 70 µm. In some embodiments, the water droplets in the blended sample have an average diameter of about 50 µm.

In another embodiment of the invention, the low water content fluid is blended prior to collecting the sample, such that the method begins with the step of obtaining the blended sample of the low water content fluid. In some embodiments, the blended sample is obtained by transferring the blended sample to a measurement vessel installed in a process stream.

In the step of transferring the portion of the blended sample to cuvette 102 to create measurement sample 130, the portion of the blended sample which is transferred to cuvette 102 can be some or all of the blended sample. One of skill in the art will appreciate that the volume of the portion of the blended sample transferred to cuvette 102 is dependent on the size of cuvette 102. The blended sample can be transferred to cuvette 102 by an eyedropper, a pipette, tubes, hoses, pipes, a by-pass line, and the like. Alternately, the blended sample may be transferred to a designated section of a process stream where cuvette 102 is located, in one embodiment, a portion of the blended sample having a volume of about 3 mL to about 4 mL is transferred to cuvette 102 using an eyedropper to create measurement sample 130.

Viewing surface 106 of cuvette 102 is covered with opaque sheet 114 containing slit 116 to form the covered side of cuvette 102. Cuvette 102 includes laser-receptive surface 104 adjacent to viewing surface 106. In some embodiments, opaque sheet 114 covers a portion of viewing surface 106 and inhibits the laser-induced fluorescence that is measured by spectrometer 124. In at least one embodiment, opaque sheet 114 is located near viewing surface 106 of cuvette 102 without being in direct contact with viewing surface 106. Slit 116 is capable of confining the area from which fluorescence 112 emits on the covered side of cuvette 102. In one embodiment slit 116 is about 0.5 mm wide.

In some embodiments of the present invention, barrier 118 having fixed opening 120 is provided between laser source 108 and laser-receptive surface 104 of cuvette 102. Barrier 118 is capable of preventing some of the electromagnetic radiation generated by laser source 108 from passing through barrier 118. Barrier 118 can be provided by any means known to one of skill in the art. In some embodiments, barrier 118 is provided as a thin wall. In other embodiments, barrier 118 is provided as a section of a container. In still further embodiments, barrier 118 is provided as a coating applied to cuvette 102. Barrier 118 contains fixed opening 120. Fixed opening 120 can be configured to transmit at least some of pulsed laser beam 110 to laser-receptive surface 104 of cuvette 102. Fixed opening 120 can be of any shape or size. In at least one embodiment, fixed opening 120 has a circular cross-section and has a diameter of about 0.5 mm. In some embodiments, fixed opening 120 is capable of preventing some wavelengths of electromagnetic radiation from being transmitted from laser source 108 to laser-receptive surface 104.

In the step of transmitting pulsed laser beam 110 through laser-receptive surface 104, pulsed laser beam 110 is generated by laser source 108 and directed through fixed opening 120 and through laser-receptive surface 104 of cuvette 102. In some embodiments, laser source 108 has a Q-switch and pulsed laser beam 110 is a Q-switched laser beam. In at least one embodiment, pulsed laser beam 110 is transmitted through laser-receptive surface 104 in the form of laser pulses, each laser pulse having a temporal span of 6 ns/pulse and at an energy of about 20 mJ/pulse. Pulsed laser beam 110 has a wavelength operable to induce fluorescence in measurement sample 130. In some embodiments, pulsed laser beam 110 has a wavelength in the range of UV light (usually between about 250 nm and about 400 nm). In at least one embodiment, pulsed laser beam 110 has a wavelength of about 266 nm. Additional steps can be performed on pulsed laser beam 110 prior to being transmitted through laser-receptive surface 104 of cuvette 102. In at least one embodiment, barrier 118 blocks a portion of pulsed laser beam 110 and fixed opening 120 allows another portion of pulsed laser beam 110 to pass through to laser-receptive surface 104 of cuvette 102. In some embodiments, barrier 118 is used to shield cuvette 102 from electromagnetic radiation. Laser-receptive surface 104 allows pulsed laser beam 110 to pass into cuvette 102 and irradiate measurement sample 130. In some embodiments, laser-receptive surface 104 prevents the transmission of some electromagnetic radiation into cuvette 102 while allowing other electromagnetic radiation to pass through laser-receptive surface 104 and into cuvette 102.

In the step of inducing fluorescence in the fluorescence spectrum of measurement sample 130, pulsed laser beam 110 passes through laser receptive surface 104 of cuvette 102 to irradiate measurement sample 130. Laser-induced fluorescence is produced when measurement sample 130 absorbs the electromagnetic radiation from pulsed laser beam 110 and emits light with a longer wavelength than that of the absorbed electromagnetic radiation. The laser-induced fluorescence is emitted across the fluorescence spectrum corresponding to the range of wavelengths at which measurement sample 130 fluoresces. In some embodiments, a first portion of the laser-induced fluorescence passes through slit 116 on the covered side of cuvette 102 while opaque sheet 114 prevents a second portion of the laser-induced fluorescence from being emitted from the covered side of cuvette 102. Slit 116 can be of any size and shape allowing fluorescence 112 to be emitted from slit 116. In some embodiments, slit 116 only allows the laser-induced fluorescence excited in certain locations within cuvette 102 to pass through slit 116. In at least one embodiment, slit 116 is arranged such that pulsed laser beam 110 excites measurement sample 130 and fluorescence 112 emits through slit 116 in about a 90° excitation-emission geometrical configuration. Fluorescence 112 emitted from slit 116 can then be collected and focused through collecting lens 122 and transmitted to spectrometer 124 for measurement.

In the step of focusing fluorescence 112 through collecting lens 122, collecting lens 122 is located between cuvette 102 and spectrometer 124. In some embodiments, fluorescence 112 emitted from slit 116 is refracted as it passes through collecting lens 122. As described above, collecting lens 122 collects and focuses fluorescence 112, and is capable of increasing the intensity of the fluorescence measured by spectrometer 124. In some embodiments, collecting lens 122 focuses fluorescence 112 into a point on spectrometer 124. Alternately, collecting lens 122 collimates fluorescence 112. Collecting tens 122 can be of any shape or material capable of bending and transmitting light. In one embodiment, quartz lenses collect and focus fluorescence 112 emitted from slit 116 onto the detector of the spectrometer 124.

In the step of measuring the fluorescence with spectrometer 124, some or all of fluorescence 112 that is transmitted through collecting lens 122 is detected by spectrometer 124. Spectrometer 124 can have any configuration known to one skilled in the art to be capable of measuring an incoming electromagnetic wave. Spectrometer 124 can include spectrograph 126 containing the detector. Spectrometer 124 can measure the intensity of fluorescence 112 by dispersing the incoming fluorescence received by the detector and displaying the fluorescence intensity across the fluorescence spectrum of the sample. In some embodiments, spectrograph 126 disperses the incoming fluorescence with a resolution of about 3 nm. In some embodiments, the fluorescence spectrum is in a range between about 280 nm and about 450 nm. In further embodiments, the range of the fluorescence spectrum is between about 355 nm and about 375 nm. Spectrometer 124 can also include ICCD 128. In accordance with some embodiments, ICCD 128 intensifies the incoming fluorescence dispersed by spectrograph 126 and outputs a signal of the fluorescence intensity of measurement sample 130. Spectrometer 124 can measure the fluorescence at any feasible sampling rate. In some embodiments, ICCD 128 intensifies and measures the incoming fluorescence dispersed by spectrograph 126 in 25 ns intervals. In at least one embodiment, ICCD 128 is triggered by the Q-switch of laser source 108 such that it is synchronized with pulsed laser beam 110.

Figure 2:
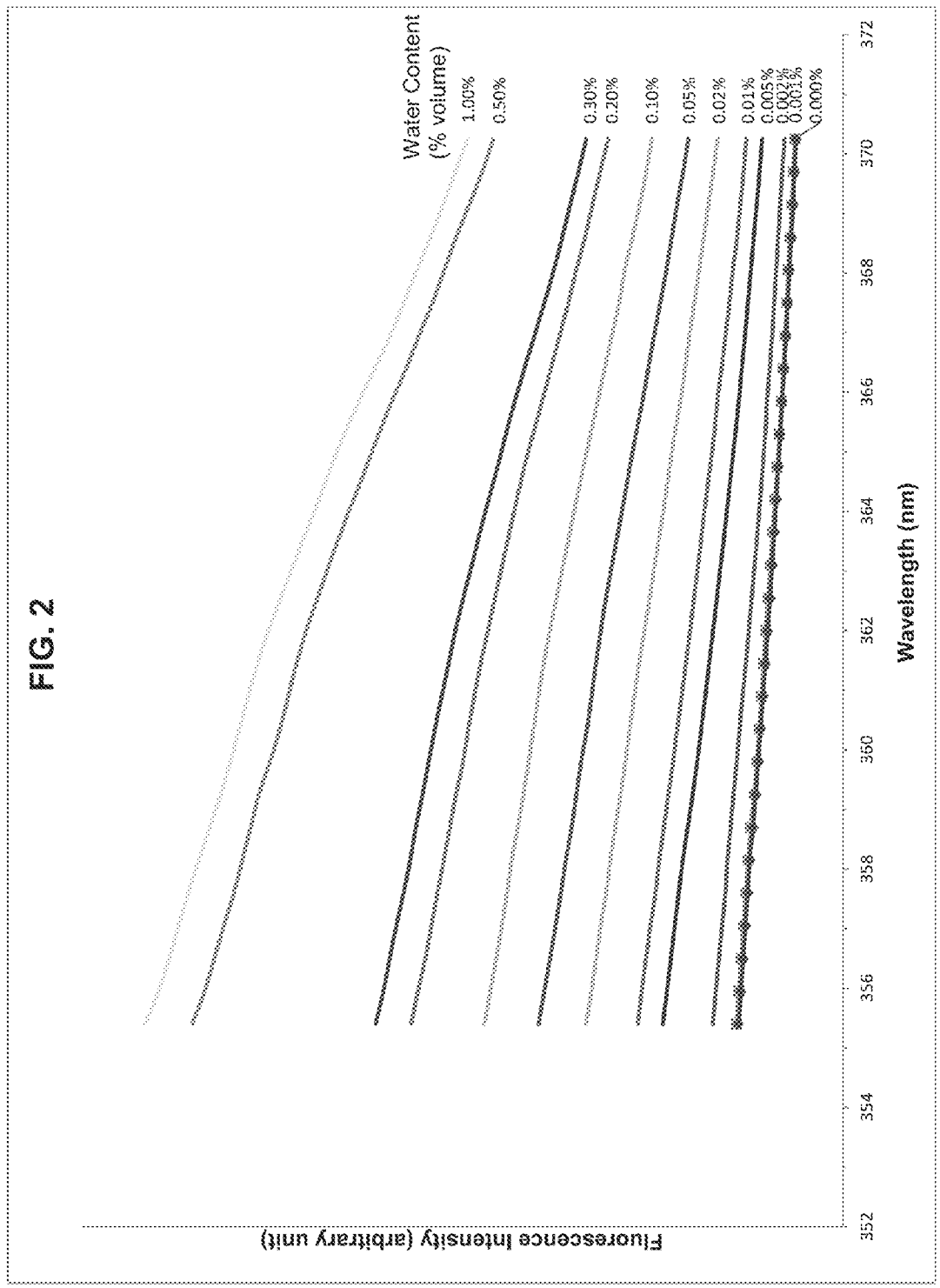
FIG. 2 is a graph of the relative fluorescence spectra in the range between 352 nm and 372 nm for kerosene having a water content in a range between 0.001% and 1% by volume, measured according to an embodiment of the present invention.
Figure 3:
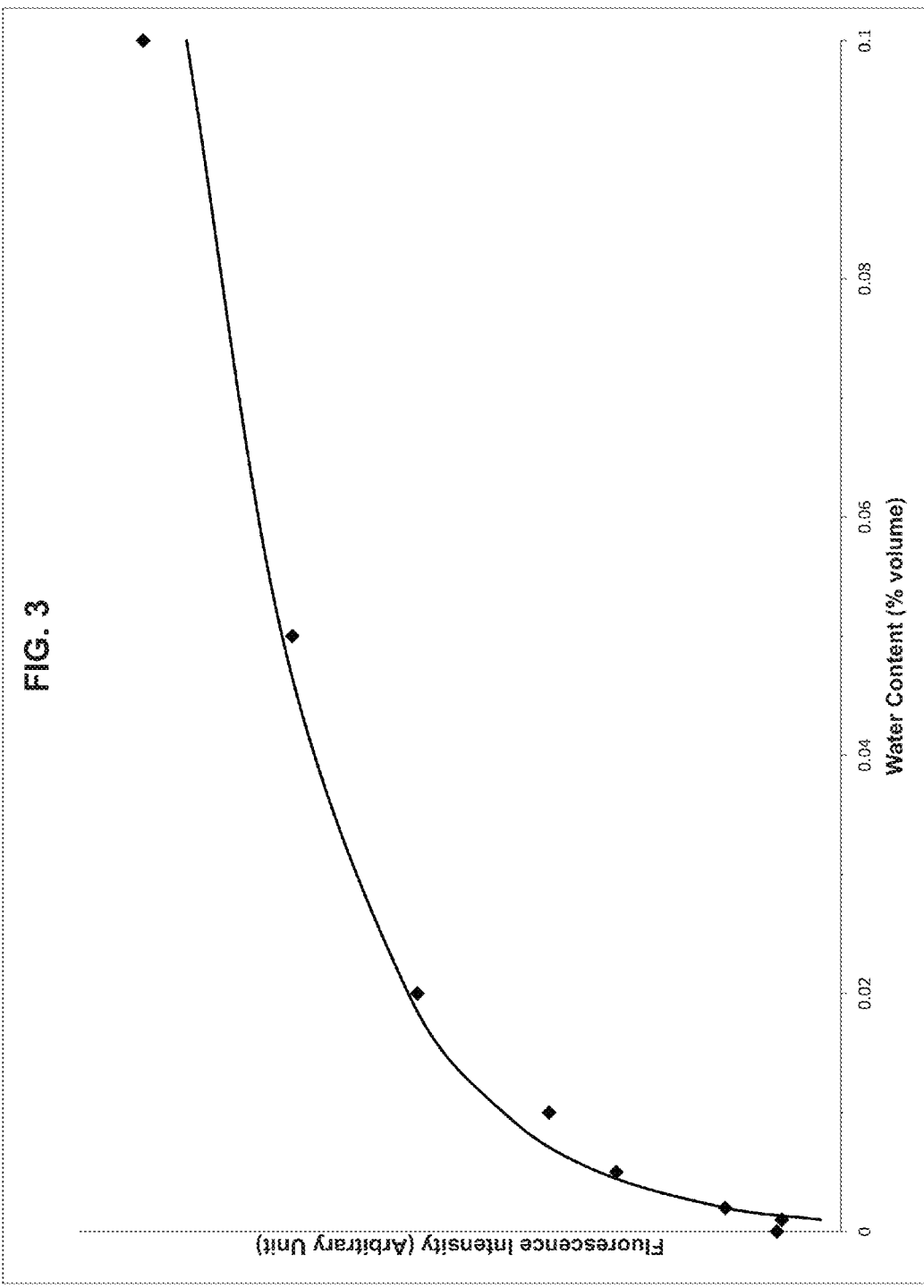
FIG. 3 is a plot of the intensity of the fluorescence spectrum (based on a fluorescence spectrum range of 352 nm to 372 nm) for kerosene having a water content in a range between 0.001% and 0.1% by volume, and a logarithmic line of best fit.
Figure 4:
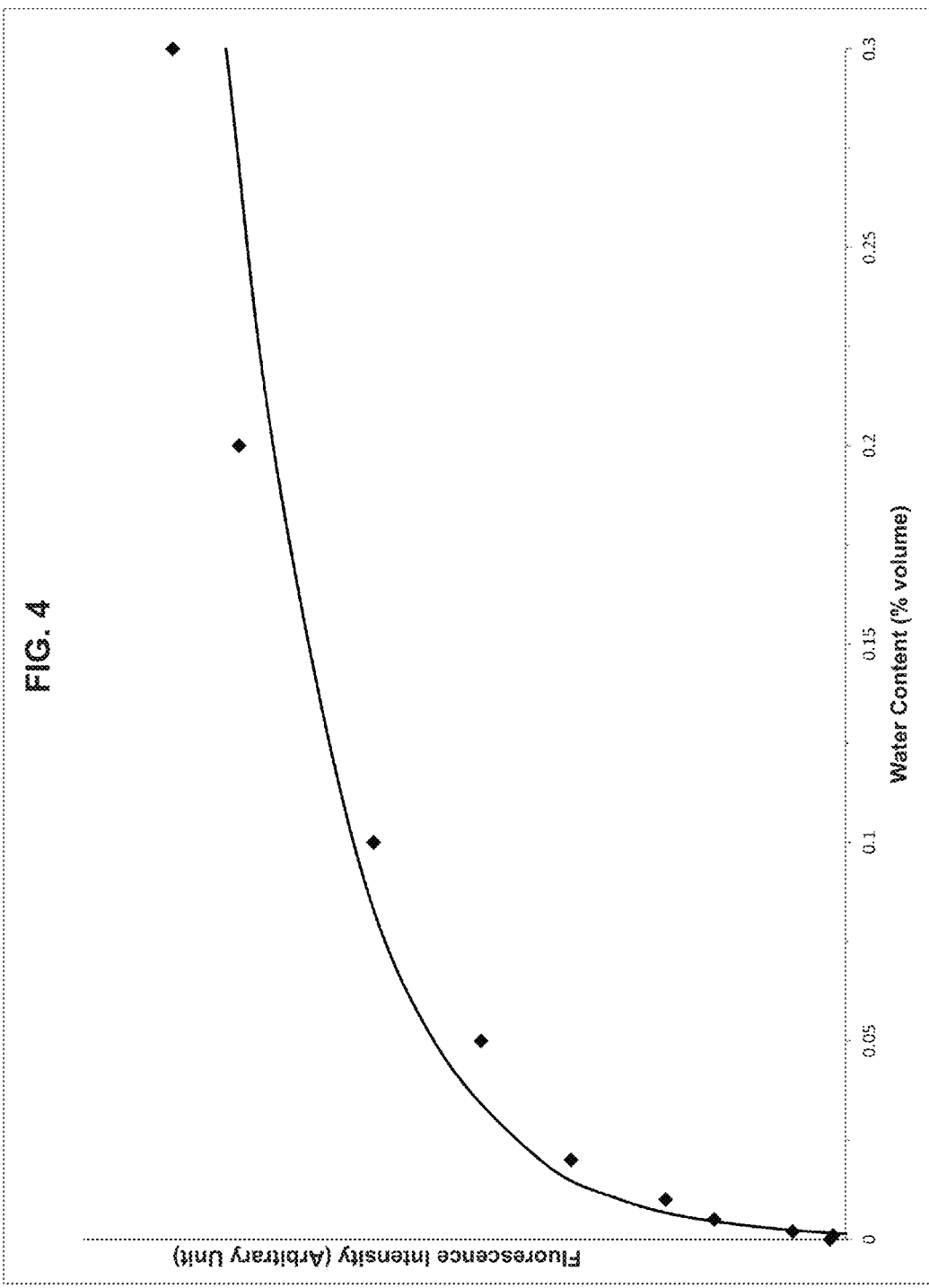
FIG. 4 is a plot of the intensity of the fluorescence spectrum (based on a fluorescence spectrum range of 352 nm to 372 nm for kerosene having a water content in a range between 0.001% and 0.3% by volume, and a logarithmic line of best fit.
Figure 5:
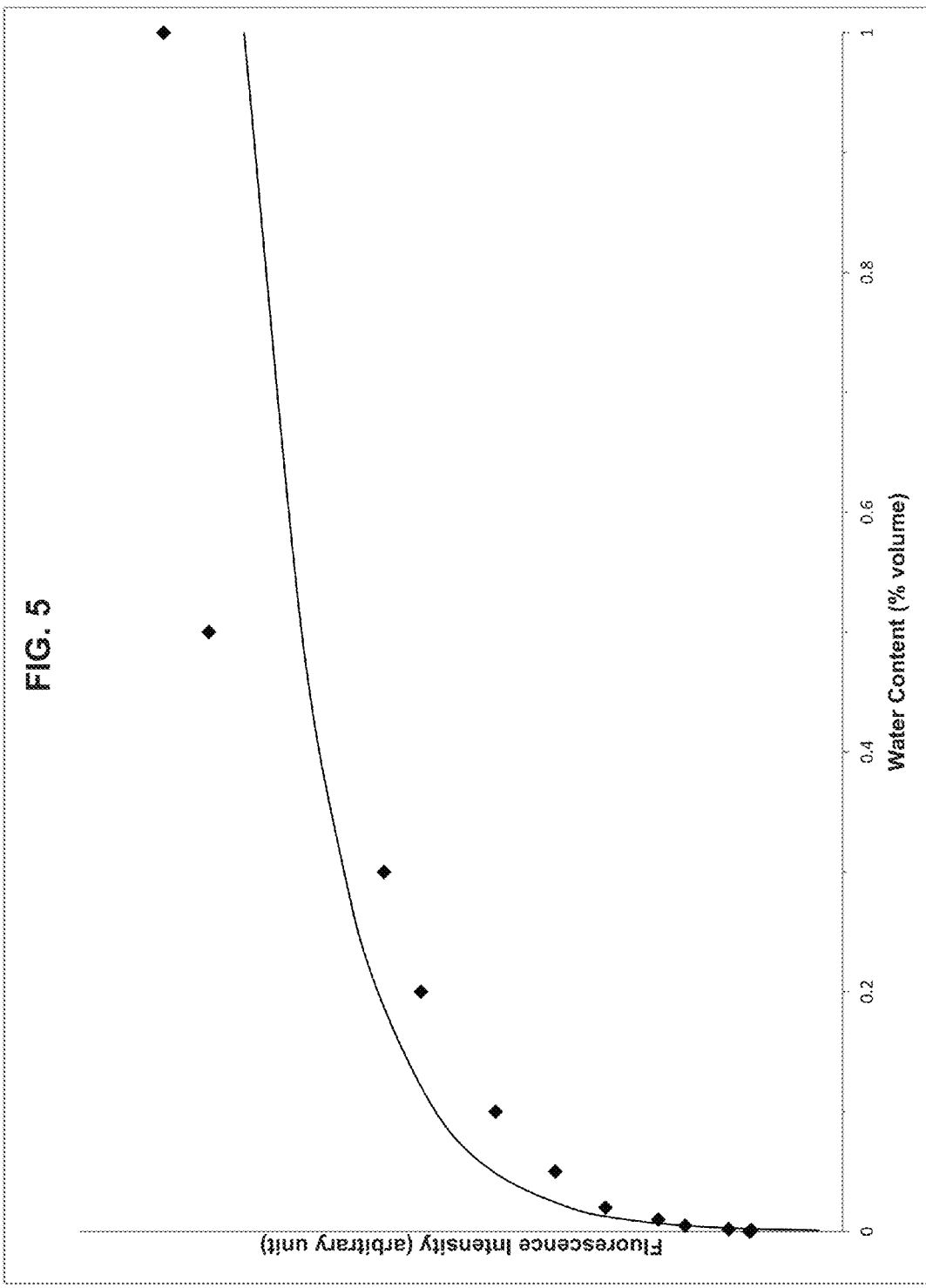
FIG. 5 is a plot of the intensity of the fluorescence spectrum (based on a fluorescence spectrum range of 352 nm to 372 nm) for kerosene having a water content in a range between 0.001% and 1% by volume, and a logarithmic line of best fit.

As depicted in FIG. 2, spectrometer 124 can measure the fluorescence intensity at each wavelength in the fluorescence spectrum of fluorescence 112, forming a plot of the fluorescence intensity of the sample. The plot of the fluorescence intensity can be displayed using any feasible method known to one skilled in the art. In some embodiments, the plot is displayed on a computer monitor using convenient software. Alternately, the plot may be stored on a machine readable medium or used by other methods known to one skilled in the art. The fluorescence intensity of the sample is directly proportional to the amount of water in the low water content fluid. As depicted in FIGS. 3-5, the fluorescence intensity can be approximated by a logarithmic function for at least an amount of water in the range between about 0.001% and about 1% by volume.

In another aspect of the invention, the method allows the overall water distribution of the sample of low water content fluid to be mapped by taking additional portions of the sample and measuring the additional portions with spectrometer 124. The additional portions can be taken from the sample either prior to blending the sample or subsequent to blending the sample. In some embodiments, the additional portions are taken from different locations in the blended sample. The additional portions can be taken from the top, bottom, front, back, center, and edges of the sample. Alternately, the additional portions can be taken from the sample periodically over a given time interval. The sample of the low water content fluid can be mapped for any purpose related to determining the presence of water in an oil-containing fluid. Exemplary purposes include determining characteristics such as local water concentration at multiple locations in the low water content fluid, determining the overall amount of water in the low water content fluid, determining characteristics such as local water concentration in a water-in-oil emulsion flow, mapping a flow process over a period of time, mapping of water contamination in storage tanks, and determining the effect of parameters such as temperature and pressure on the amount of water in the sample, among other uses known to one skilled in the art. In some embodiments, the additional portions are taken from blended samples having different known amounts of water to create a calibration curve based on the fluorescence intensity of the low water content fluid.

The examples below incorporate the same operating conditions as additional portions are taken from the sample. In some embodiments, cuvette 102 is flushed before taking additional portions of the sample. Calibration of some or all of apparatus 100 is performed before taking additional portions of the sample. In some embodiments, the voltage across ICCD 128 is maintained at a constant level when measuring the additional portions of the sample. The fluorescence intensity of each portion of the sample can be integrated over any range of the fluorescence spectrum to create an integrated fluorescence intensity. The integrated fluorescence intensity can be plotted as a function of the amount of water in the sample.

In a further embodiment, the water concentration of the sample may be monitored in real-time, owing to the non-intrusive nature of the measurement technique contemplated by the present invention. In one embodiment, an on-line application using a bypass arrangement to bypass a main process line. The bypass arrangement line has an optical window (for example, square or oval/circular) such that pulsed laser beam 110 irradiates one surface and spectrometer 124 is positioned between 60 and 120° from the optical window.

EXAMPLES

Example 1

In Example 1, the oil-containing fluid was jet fuel grade kerosene. The sample of low water content fluid was created by collecting a sample of the jet fuel grade kerosene in a 1000 mL beaker and adding an amount of water. A pipette was used to add a known amount of distilled water to the jet fuel grade kerosene to create a low water content fluid having 7000 ppm water (corresponding to an amount of water of 1% by volume). The amount of water in the sample was controlled by using pipettes to add distilled water to the kerosene sample. A high-speed handheld blender was used to blend the sample by setting an angular speed of the mixing rotor of the blender to 13,500 rpm and allowing the sample to mix for a duration of 2 minutes. At the end of the blending step, the sample contained water droplets with a size distribution of 30 μm to 70 μm in diameter, with an average diameter of 50 μm. After the sample was blended, an eyedropper was used to take between 3 mL and 4 mL from the approximate center of the blended sample and transfer the volume to a quartz cuvette. The viewing surface of the quartz cuvette was covered with an opaque thin metallic sheet with a narrow slit. The narrow slit was 0.5 mm wide and located 4 mm from the edge of the quartz cuvette joining the viewing surface and the laser-receptive surface. A Q-switched laser beam with a wavelength of 266 nm was used to irradiate the quartz cuvette. The Q-switch was calibrated to produce laser beam pulses with an energy of 20 mJ/pulse and a temporal span of 6 ns/pulse. The Q-switched laser beam was directed through the fixed opening of the barrier, which reduced the diameter of the laser beam to 0.5 mm. The Q-switched laser beam irradiated the cuvette, inducing fluorescence in the measurement sample within the cuvette. The narrow slit in the opaque sheet was configured such that the laser-induced fluorescence emitted from the narrow slit at an angle of 90° from the vector at which the Q-switched laser beam was directed into the cuvette. The spectrometer included a spectrograph coupled with an ICCD. The fluorescence emitted from the narrow slit passed through the collection lens, which focused the fluorescence onto the detector of the spectrograph. The spectrograph dispersed the light transmitted from the collection lens to create a fluorescence signal in the fluorescence spectrum at a resolution of 3 nm. The fluorescence spectrum for the sample was between 280 nm and 450 nm. The Q-switch of the laser source was configured to trigger a sensor on the ICCD, allowing the ICCD to measure the fluorescence signal received from the spectrograph. The ICCD sensed the fluorescence signal during a 25 ns time window after each pulse of the Q-switched laser beam. The fluorescence signal measured by the ICCD was then displayed on a computer monitor.

Example 2

In Example 2, the fluorescence measurement process of Example 1 was repeated under identical conditions for samples having amounts of water of 7 ppm, 14 ppm, 35 ppm, 70 ppm, 140 ppm, 210 ppm, 350 ppm, 700 ppm, 1400 ppm, 3500 ppm, and 7000 ppm (corresponding to an amount of water in the low water content fluid of 0.001%, 0.002%, 0.005%, 0.01%, 0.02%, 0.05%, 0.1%, 0.2%, 0.5%, and 1% by volume, respectively). A volumetric water content between 0.001% and 1.00% corresponds to a water content in the sample between 7 ppm and 7000 ppm. For each sample, the fluorescence intensity of the sample was measured. FIG. 2 is a plot of the fluorescence intensity of each of the samples over a range of the fluorescence spectrum having wavelengths between 355 nm and 375 nm. The fluorescence intensity was integrated over the range of the fluorescence spectrum shown in FIG. 2 and plotted in three ranges corresponding to three orders of water content in the samples. The first range included samples with amounts of water between 7 ppm and 700 ppm, the second range included samples with amounts of water between 7 ppm and 2100 ppm, and the third range included samples with amounts of water between 7 ppm and 3500 ppm. A logarithmic line of best fit was overlaid on the plot of the integrated fluorescence intensities for samples having amounts of water within each range.

FIG. 3 is a display of the integrated fluorescence intensities of samples having amounts water in the range between 7 ppm and 700 ppm, together with the line of best fit for this range. This corresponds to a range of water in oil between 0.001% to 0.1% by volume. The coefficient of determination for the line of best fit in FIG. 3 was 0.98, and the estimated error for determining the amount of water based on fluorescence intensity was ±3 ppm.

FIG. 4 is a display of the integrated fluorescence intensities for samples having amounts of water between 7 ppm and 2100 ppm, together with the line of best fit for this range. The range corresponds to a range of water in oil between 0.001% and 0.3% by volume. The coefficient of determination for the line of best fit in FIG. 4 was 0.97 and the estimated error was ±5 ppm.

FIG. 5 is a display of the integrated fluorescence intensities for samples having amounts of water between 7 ppm and 7000 ppm, together with the line of best fit for this range. The coefficient of determination for the line of best fit in FIG. 5 was 0.92 and the estimated error was ±200 ppm.

Although the present invention has been described in detail, it should be understood that various changes, substitutions, and alterations can be made hereupon without departing from the principle and scope of the invention. Accordingly, the scope of the present invention should be determined by the following claims and their appropriate legal equivalents.

The singular forms "a," "an," and "the" include plural referents, unless the context clearly dictates otherwise.

Ranges may be expressed herein as from about one particular value, and/or to about another particular value. When such a range is expressed, it is to be understood that another embodiment is from the one particular value and/or to the other particular value, along with all combinations within said range.

As used herein, terms such as "first" and "second" are arbitrarily assigned and are merely intended to differentiate between two or more components of an apparatus. It is to be understood that the words "first" and "second" serve no other purpose and are not part of the name or description of the component, nor do they necessarily define a relative location or position of the component. Furthermore, it is to be understood that that the mere use of the term "first" and "second" does not require that there be any "third" component, although that possibility is contemplated under the scope of the present invention.

What is claimed is:

1. A method for determining trace amounts of water in oil, the method comprising the steps of:
    obtaining a blended sample of a low water content fluid, wherein the low water content fluid comprises an amount of water and an amount of oil, and wherein the amount of water in the blended sample is distributed as water droplets, the water droplets having an average diameter in a range between 30 µm and 70 µm such that the blended sample is a stable emulsion;
    transferring a portion of the blended sample to a cuvette to create a measurement sample, the cuvette having a laser-receptive surface adjacent to a viewing surface, the viewing surface of the cuvette having an opaque sheet applied thereto to form a covered side, wherein the opaque sheet contains a slit such that the position of the slit is fixed for all measurements, wherein the slit if 0.5 mm wide;
    transmitting a pulsed laser beam from a laser source through the laser-receptive surface of the cuvette;
    inducing fluorescence in a fluorescence spectrum of the measurement sample, wherein the pulsed laser beam induces fluorescence, and wherein the fluorescence emits from the slit in the opaque sheet on the covered side of the cuvette;
    focusing the fluorescence through a collecting lens and transmitting the fluorescence to a spectrometer, wherein the collecting lens is located between the cuvette and the spectrometer, wherein the spectrometer comprises a spectrograph coupled with an intensified charge coupled device; and
    measuring the fluorescence with the spectrometer, comprising the steps of:
        dispersing the fluorescence with the spectrograph; and
        intensifying the fluorescence with the intensified charge coupled device.

2. The method of claim 1, further comprising the steps of providing a barrier located between the laser source and the laser-receptive surface of the cuvette, the barrier defining a fixed opening; and
    transmitting the pulsed laser through the fixed opening prior to transmitting the laser through the laser-receptive surface of the cuvette.

3. The method of claim 1, wherein the pulsed laser beam has a wavelength of 266 nm.

4. The method of claim 1, wherein the fluorescence spectrum is in a range between 280 nm and 450 nm.

5. The method of claim 1, wherein the pulsed laser beam pulses for a temporal span of 6 ns/pulse at an energy of 20 mJ/pulse.

6. The method of claim 1, wherein the slit is 4 mm from an edge of the cuvette joining the laser receptive surface and the viewing surface.

7. The method of claim 1, wherein the oil is jet fuel.

8. The method of claim 1, further comprising the steps of collecting a sample of the low water content fluid; and blending the sample to create the blended sample.

9. The method of claim 1, further comprising the steps of
taking additional portions from the blended sample at different locations of the blended sample; and
measuring the fluorescence of the additional portions with the spectrometer,
wherein the measurements of the fluorescence of the additional portions give the ability to map the entire blended sample.

10. The method of claim 1, wherein the fluorescence spectrum of the measurement sample as measured by the spectrometer is in a range between 355 nm and 375 nm.

\* \* \* \* \*